US009110251B2

(12) United States Patent
Chen et al.

(10) Patent No.: US 9,110,251 B2
(45) Date of Patent: Aug. 18, 2015

(54) PROCESSING IMAGES OF FIBER OPTIC CONNECTOR ENDS

(75) Inventors: David Zhi Chen, Richardson, TX (US); William Johnston, Jr., Baltimore, MD (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 710 days.

(21) Appl. No.: 13/307,466

(22) Filed: Nov. 30, 2011

(65) Prior Publication Data
US 2013/0138362 A1    May 30, 2013

(51) Int. Cl.
*G02B 6/42*    (2006.01)
*G01N 21/88*    (2006.01)
*G02B 6/38*    (2006.01)
*G01N 21/958*    (2006.01)
G01N 21/53    (2006.01)
G01N 21/94    (2006.01)
G01N 21/95    (2006.01)

(52) U.S. Cl.
CPC .............. *G02B 6/385* (2013.01); *G01N 21/958* (2013.01); *G01N 21/534* (2013.01); *G01N 21/94* (2013.01); *G01N 2021/9511* (2013.01)

(58) Field of Classification Search
CPC ...... G02B 6/42; G02B 6/4246; G02B 6/2804; G02B 6/2821; G02B 6/4204; G02B 6/3885; G02B 6/4296; G01N 21/88; G01N 21/94; G01N 2021/9511

USPC .......... 702/40, 33–36, 81, 84, 127, 150–153, 702/182–183, 189; 356/73.1, 138, 356/139.04–139.08, 150, 152.1, 153, 356/237.1–237.3, 239.2, 239.7–239.8, 356/600–601; 382/108, 141, 145–146, 382/148–149, 151–152; 385/60, 72, 76–78, 385/85, 97, 134
See application file for complete search history.

(56) References Cited

U.S. PATENT DOCUMENTS 7,356,236 B1 * 4/2008 Huang et al. .................. 385/134

OTHER PUBLICATIONS

Bhoite et al., Automated Fiber Optic Cable Endface Field Inspection Technology, Sep. 12-15, 2011, AUTOTESTCON 2011 IEEE, 9 pp.*
Abstract of Bhoite et al. reference, Sep. 12-15, 2011, 2 pp.*
Berdinskikh et al., Development of Cleanliness Specifications for Single-Mode Connectors with 1.25 and 2.5 mm Ferrules, 2005 Optical Society of America, 10 pp.*

* cited by examiner

Primary Examiner — Toan Le

(57) ABSTRACT

A system includes a scope for obtaining images of an end face of an optical fiber in a fiber optic connector. The system also includes a computing device. The computing device is configured to obtain images of the end face of the optical fiber via the scope, identify surface defects on the end face of the optical fiber based on the images, and determine insertion loss of the fiber optic connector due to the surface defects.

21 Claims, 10 Drawing Sheets

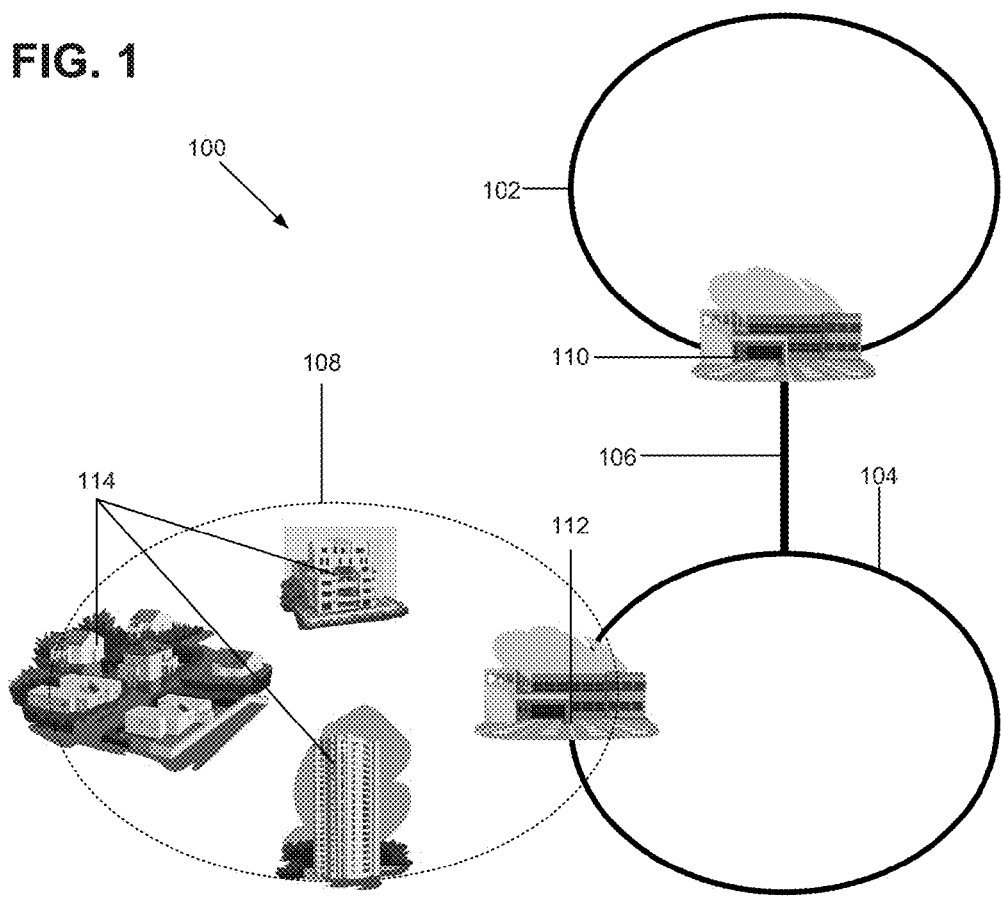

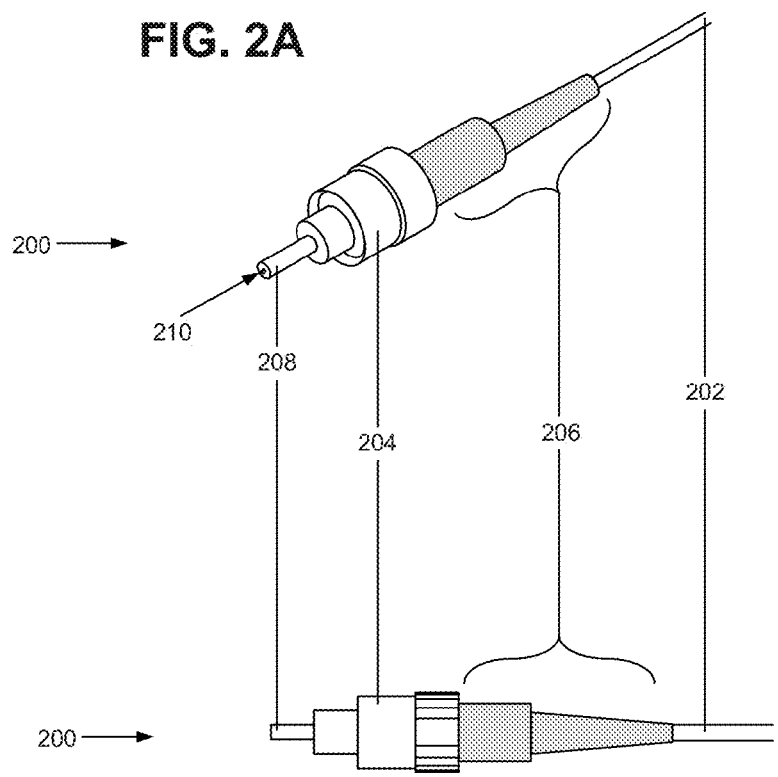
FIG. 2A
FIG. 2B
FIG. 2C
FIG. 2D

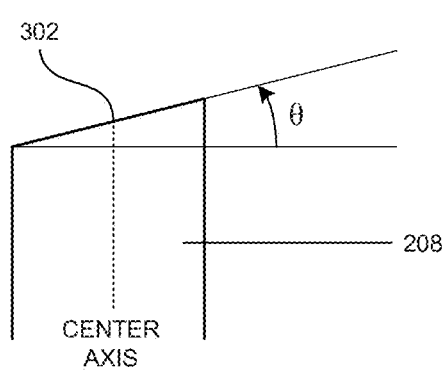
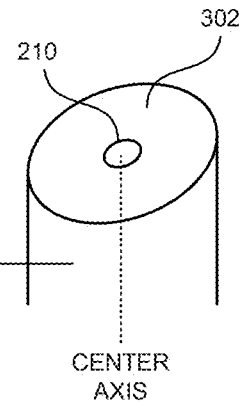
FIG. 3A　　　　　　　　　FIG. 3B
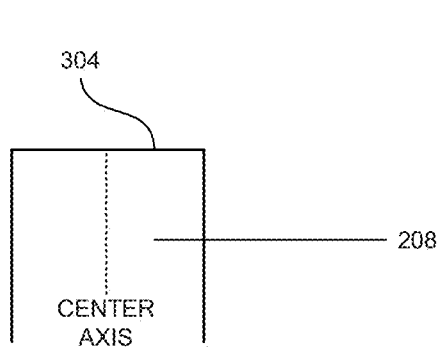
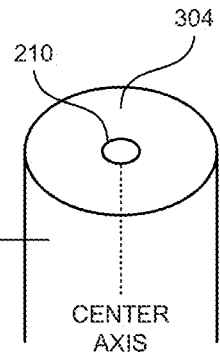
FIG. 3C　　　　　　　　　FIG. 3D

PROCESSING IMAGES OF FIBER OPTIC CONNECTOR ENDS

BACKGROUND INFORMATION

Optical signals that travel from a central office to customer premises over optical fibers (beyond 20~50 kilometers) will be attenuated due to fiber loss and distorted due to optical dispersion. In some instances, fiber loss occurs when optical signals transition from one optical fiber to another optical fiber via a fiber optic connector that aligns and secures the optical fiber ends. To ensure the integrity of optical signals, an engineer or a technician may test fiber optic connectors for cleanliness of and possible damages to optical fiber ends inside the fiber optic connector.

BRIEF DESCRIPTION OF THE DRAWINGS

FIG. 1 illustrates an exemplary optical network in which fiber optic connectors may be used;

FIGS. 2A and 2B are a perspective view and a side view, respectively, of an exemplary fiber optic connector;

FIGS. 2C and 2D are cross-sectional views of an optical fiber in the fiber optic connector of FIGS. 2A and 2B according to different embodiments;

FIGS. 3A and 3B are a side view and a perspective view, respectively, of the ferrule of FIG. 2A according to one embodiment;

FIGS. 3C and 3D are a side view and a perspective view, respectively, of the ferrule of FIG. 2A according to another embodiment;

DETAILED DESCRIPTION OF PREFERRED EMBODIMENTS

Figure 4A:
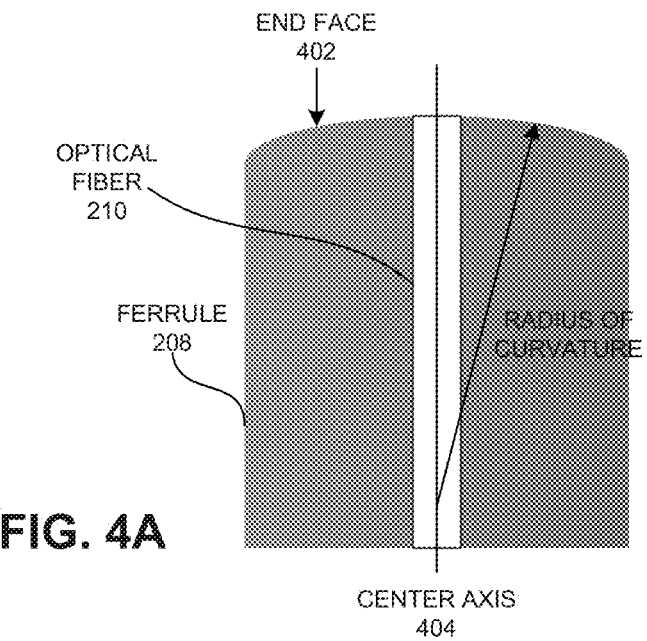
FIG. 4A is a cross-sectional view of the ferrule of FIGS. 2A and 2B according to another implementation.

The following detailed description refers to the accompanying drawings. The same reference numbers in different drawings may identify the same or similar elements. As used herein, the term "opacity" of a medium may refer to the extent by which an optical signal (e.g., light) is impeded, due to optical properties of the medium, from propagating through the medium. In contrast, as used herein, the term "clarity" of a medium may refer to ease with which an optical signal may propagate through the medium.

As described below, a system may process images of end faces of optical fibers housed in fiber optic connectors. Given a fiber optic connector, the system may determine the type of optical contact associated with the fiber optic connector (e.g., angle polished contact (APC), ultra polished contact (UPC), etc.); may position the fiber optic connector for imaging; may determine the type of optical fiber inside the fiber optic connector (e.g., single mode fiber, multimode fiber, etc.); and may determine the opacity of the end face of the optical fiber inside the fiber optic connector. The system may determine the opacity by processing one or more images of the end face. The image processing may include identifying scratches, damages, and/or other surface defects or characteristics that impede propagation of optical signals through the end face.

FIG. 1 shows an exemplary optical network 100 in which fiber optic connectors may be used. As shown, optical network 100 may include metro/regional networks 102 and 104, long haul or ultra-long haul optical lines 106, and edge network 108. Depending on the implementation, optical network 100 may include additional, fewer, or different optical networks and optical lines than those illustrated in FIG. 1. For example, in one implementation, optical network 100 may include additional edge networks and/or metro/regional networks that are interconnected by Synchronous Optical Network (SONET) rings.

Metro/regional network 102 may include optical fibers and central office hubs that are interconnected by the optical fibers. The optical fibers, which may form the backbone of metro/regional network 102, may span approximately 50 to 500 kilometers (km). The central office hubs (also called "central office"), one of which is illustrated as central office hub 110, may include sites that house telecommunication equipment, including switches, optical line terminals, etc. In addition to being connected to other central offices, central office hub 110 may provide telecommunication services to subscribers, such as telephone service, access to the Internet, television service, etc., via optical line terminals.

Metro/regional network 104 may include similar components as metro/regional network 102. Network 104 may operate similarly as network 102. In FIG. 1, metro/regional network 104 is illustrated as including central office hub 112, which may include similar components as central office hub 110. Central office hub 112 may operate similarly as central office hub 110.

Long haul optical lines 106 may include optical fibers that extend from metro/regional optical network 102 to metro/regional network 104. In some implementations, long haul optical lines 106 may span approximately 500 km or more, with proper in-line optical amplifiers and wavelength division multiplexed (WDM) transponders.

Edge network 108 may include optical networks that provide user access to metro/regional network 104. As shown in FIG. 1, edge network 108 may include access points 114 (e.g., office buildings, residential area, etc.) via which end customers may obtain communication services from central office hub 112.

In network 100, fiber optic connectors may be used in each of networks 102, 104, and 108 to connect different optical fibers and equipment. For example, fiber optic connectors may interconnect long haul optical fiber cables. In another example, fiber optic connectors may connect optical fiber cables from central office hub 112 to optical fiber cables within/near access points 114.

In some implementations, the distances spanned by optical fiber cables that carry signals from central office 102 to access points 114 or customer premises may be large. Because pre-factory-made optical fiber cable lengths are set at particular values, fiber optic connectors are needed to adjoin the optical fiber cables to cover the distances.

When a fiber optic connector adjoins two optical fiber cables, the fiber optic connector aligns, abuts, and adjoins two optical fiber ends inside the optical fiber cables. Depending on the opacity of the end faces/surfaces of the optical fibers, optical signals that propagate from one of the optical fibers to the other optical fiber may suffer losses in signal strength. In some instances, the losses may be too much for the optical fiber and the fiber optic connector to be used in certain types of applications and/or systems. According to some embodiments, to determine whether the end face of the optical fiber inside a fiber optic connector meets a technical requirement, the system described herein may examine/test the end face of the optical fiber to determine its opacity.

FIGS. 2A and 2B are a perspective view and a side view, respectively, of an exemplary fiber optic connector 200. As shown, fiber optic connector 200 may include a coupling component 204, a strain relief boot 206, a ferrule 208, and a portion of optical fiber 210 (when fiber optic connector 200 is assembled with optical fiber cable 202). Depending on the implementation, fiber optic connector 200 may include additional, fewer, different, or a different arrangement of components than those illustrated in FIGS. 2A and 2B. Furthermore, although fiber optic connector 200 is illustrated as a ferrule connector/fiber channel (FC)/physical contact (PC) type connector, in another implementation, fiber optic connector 200 may include another type of connector (e.g., Standard Connector (SC) Straight tip connector (ST), Lucent Connector (LC), Mechanical Transfer (MT)-Registered jack (MT-RJ), HMS-10, DIN, a hardened MT connector, etc.). In some implementations, fiber optic connector 200 may include a protective cap/covering that may be placed over ferrule 208 and a portion of coupling component 204 when fiber optic connector 200 is not being used (i.e., when fiber optic connector 200 is not attached to another connector).

Optical fiber cable 202 may include optical fiber 210 for carrying optical signals, material surrounding optical fiber 210 (e.g., Kevlar® fiber) for providing a protective sheath around optical fiber 210, and an outer jacket. Coupling component 204 may connect fiber optic connector 200 to another connector. In addition, coupling component 204 may enclose other components, such as crimp components, etc. For example, in FIG. 2A, coupling component 204 provides space into which optical fiber 210 may be inserted.

Strain relief boot 206 may include material that protects optical fiber cable 202 and may prevent optical fiber cable 202 from bending and causing damages to optical fiber(s) in optical fiber cable 202. During the assembly of fiber optic connector 200, strain relief boot 206 may be placed over a crimp sleeve (which would have been slid over optical fibers 210 running lengthwise from an end of ferrule 208 through connector body 204 to/through optical fiber cable 202) and affixed to coupling component 204.

Ferrule 208 may include a plug that holds an end of optical fiber 210. Ferrule 208 aligns the end of optical fiber 210 to fiber optic connector 200. This allows the end of optical fiber 210 to abut the end of another optical fiber of a complementary connector attaching to fiber optic connector 200. During the assembly of fiber optic connector 200, optical fiber 210 from optical fiber cable 202 may be inserted into ferrule 208 and affixed (e.g., using epoxy) thereto. As shown in FIG. 2A, the end of optical fiber 210 is exposed at the end of ferrule 208.

In FIG. 2A, fiber optic connector 200 is attached to an optical fiber cable 202. Fiber optic connector 200 may be fitted into another fiber optic connector (e.g., a female connector), to securely provide for the end of optical fiber 210 inside ferrule 208 to securely join the end of another optical fiber in the other fiber optic connector.

FIGS. 2C and 2D are cross-sectional views of optical fiber 210 according to different embodiments. As shown, optical fiber 210 may include a core 222 and an outer portion 224, referred to as a "cladding 224," that surrounds the core and runs lengthwise inside optical fiber 210. The indices of refraction of core 222 and cladding 224 are selected to facilitate or guide a light beam to travel lengthwise in optical fiber 210.

As shown, the diameter of the core in FIG. 2I) is larger than that of the core in FIG. 2C. Whether an optical fiber can operate as a single mode fiber or a multimode fiber may depend on the diameter of the core. FIG. 2C shows optical fiber 210 implemented as a single mode optical fiber. In one implementation, the diameter of the core diameter may be approximately 8 µm. FIG. 2I) shows optical fiber 210 implemented as a multimode optical fiber. In some implementations, the diameter of the core may range approximately from 7 µm to 3,000 µm (e.g., 50 µm, 60 µm, etc.). In one implementation, the overall diameter of optical fiber 200 in FIGS. 2C and 2D is approximately 125 µm.

FIGS. 3A and 3B are a side view and a perspective view, respectively, of ferrule 208 and optical fiber 210. In FIGS. 3A and 3B, ferrule 208 includes an angle polished contact (APC) (alternatively, angle physical contact/connector (APC)). As shown, the plane of end face 302 of ferrule 208 forms an angle θ with a plane that is normal to the center axis of ferrule 208. In one implementation, θ is approximately 8 degrees.

FIGS. 3C and 3D are a side view and a perspective view, respectively, of ferrule 208 and optical fiber 210 according to another implementation. In this implementation, ferrule 208 includes a ultra polished contact (UPC) (alternatively, ultra physical connector (UPC)). As shown, the plane of end face 304 of ferrule 208 is parallel with a plane that is normal to the center axis of ferrule 208.

An APC connector (e.g., a fiber optic connector with an optical fiber having an APC) and a UPC connector (a fiber optic connector with an optical fiber having a UPC) have different optical properties. For example, in some implementations, an APC connector and a UPC connector may have different levels of insertion loss. As used herein, the term "insertion loss" may refer to the amount of optical signal power lost through the insertion of the end faces of connected optical fibers. The insertion loss may be a function of several optical fiber parameters, such as the outside diameter of the optical fiber, concentricity of the fiber cores, inside diameter of ferrule 208, the concentricity of ferrule 208, etc.

In another example, an APC connector and a UPC connector may include different levels of return loss. As used herein, the term "return loss" may refer to the amount of optical signal power lost through reflection of the optical signal at the end faces of optical fibers of an attached/mated fiber optic connector pair. For a mated UPC connector pair, return light, which results from a reflection of a forward moving light at the end faces of the optical fibers, travels straight back at the forward moving light, degrading and cross-modulating with a downstream signal. In contrast, given a mated APC connector pair, return light from the angled end faces of the optical fibers travels in a direction non-parallel to the direction of the forward moving light. The return light is absorbed by cladding 224. Accordingly, a typical, mated APC connector pair incurs less return loss than a typical, mated UPC connector pair (e.g., −65 dB return loss for an APC connector pair and −55 dB return loss for UPC connector). Similarly, a typical unmated APC connector (e.g., an APC connector at an unused port in a fiber distribution hub) may incur less return loss than an unmated UPC connector (e.g., −55 dB return loss for an unmated APC connector and −14 dB return loss for an unmated UPC connector).

FIG. 4A is a cross-sectional view of ferrule 208 according to another implementation. In FIG. 4A, ferrule 208 includes an apex cut. The side view illustrates the geometry of the end face 402 of apex cut ferrule 208 and optical fiber 210. As shown, end face 402 of ferrule 208 is curved such that the center of optical fiber is near or at the apex of end face 402. The end face is circularly symmetric with respect to angles in the plane normal to the center axis 404. As farther shown, end face 402 has a radius of curvature measured from center axis 404. Fiber optic connector 200 may use a compressive force (e.g., by spring) to adjoin connecting ends of optical fibers. The radius of curvature of ferrule 208 affects the compressive force that maintains the relative positions of the optical fibers abutting one another. If the radius of curvature is too small (e.g., <7 mm), because the abutting force between the end faces is concentrated in a relatively small contact area, the optical fibers may be prone to damages, cracks, etc. If the radius of curvature of too large (e.g., >25 mm), because the abutting force between the end faces is dispersed over a larger contact area, the optical fibers may easily become misaligned or fail to make sufficient contact with one another, resulting in increased insertion and return loss.

Figure 4B:
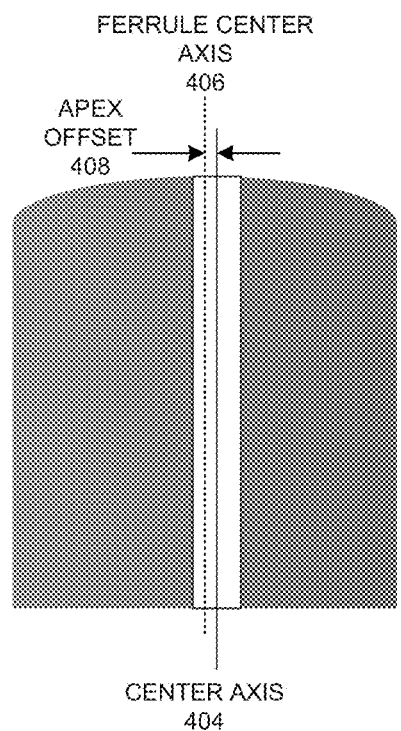
FIG. 4B illustrates an exemplary apex offset of the optical fiber of FIGS. 2A and 2B.

FIG. 4B illustrates an exemplary apex offset of optical fiber 210. As shown, center axis 404 of optical fiber 210 is offset from center axis 406 of ferrule 208, by a displacement apex offset 408. Apex offset 408 may also be the displacement between the highest point of end face 402 and center axis 404. As apex offset 408 increases (e.g., >50 μm), insertion loss and return loss at the adjoining optical fiber end faces also increase.

Figure 5A:
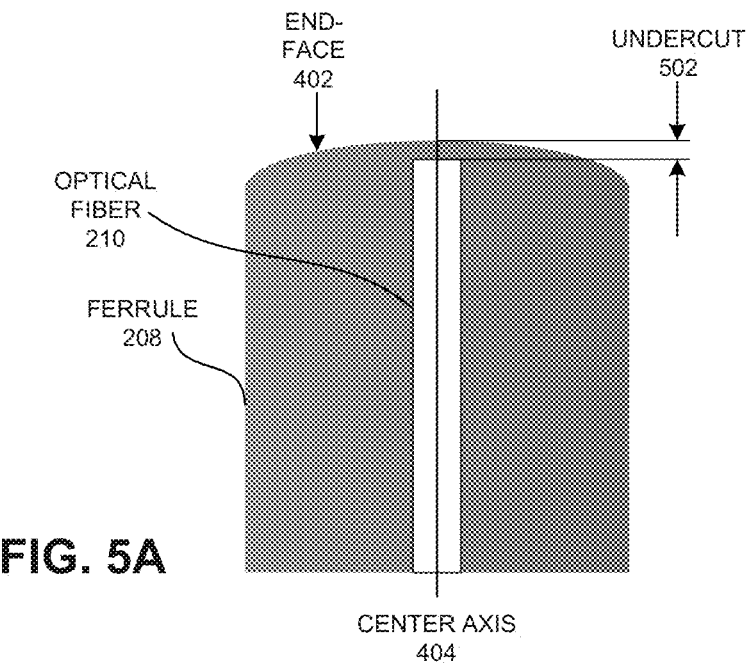
FIG. 5A depicts an exemplary undercut in the optical fiber of FIG. 4A.
Figure 5B:
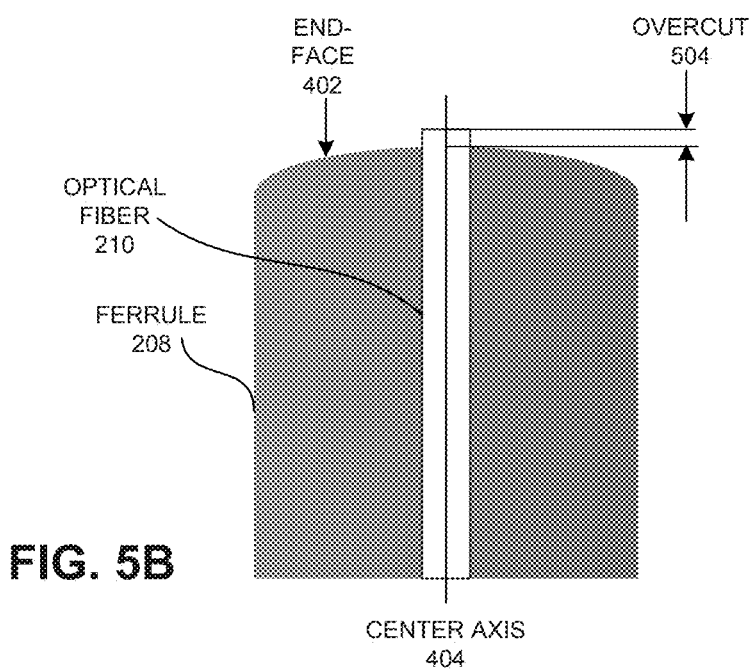
FIG. 5B depicts an exemplary overcut in the optical fiber of FIG. 4A.

FIG. 5A depicts an exemplary undercut in optical fiber 210 relative to ferrule 208. As shown, the surface of optical fiber 210 is below the surface of end face 402 near its apex, by undercut 502 amount. FIG. 5B depicts an exemplary overcut in optical fiber 210 relative to ferrule 208. As shown, the surface of optical fiber 210 is above the surface of end face 402 near the apex, by overcut 504 amount. An appropriate amount of overcut/undercut may ensure that the abutting end faces of optical fibers adjoined via a pair of fiber optic connectors will be stable. If undercut amount 502 is too large, a gap between optical fibers can result, leading to increased insertion and return losses. If overcut 504 is too large, the optical fiber end may sustain damages due to the force applied by ferrules of the pair of mated fiber optic connectors.

Figure 6A:
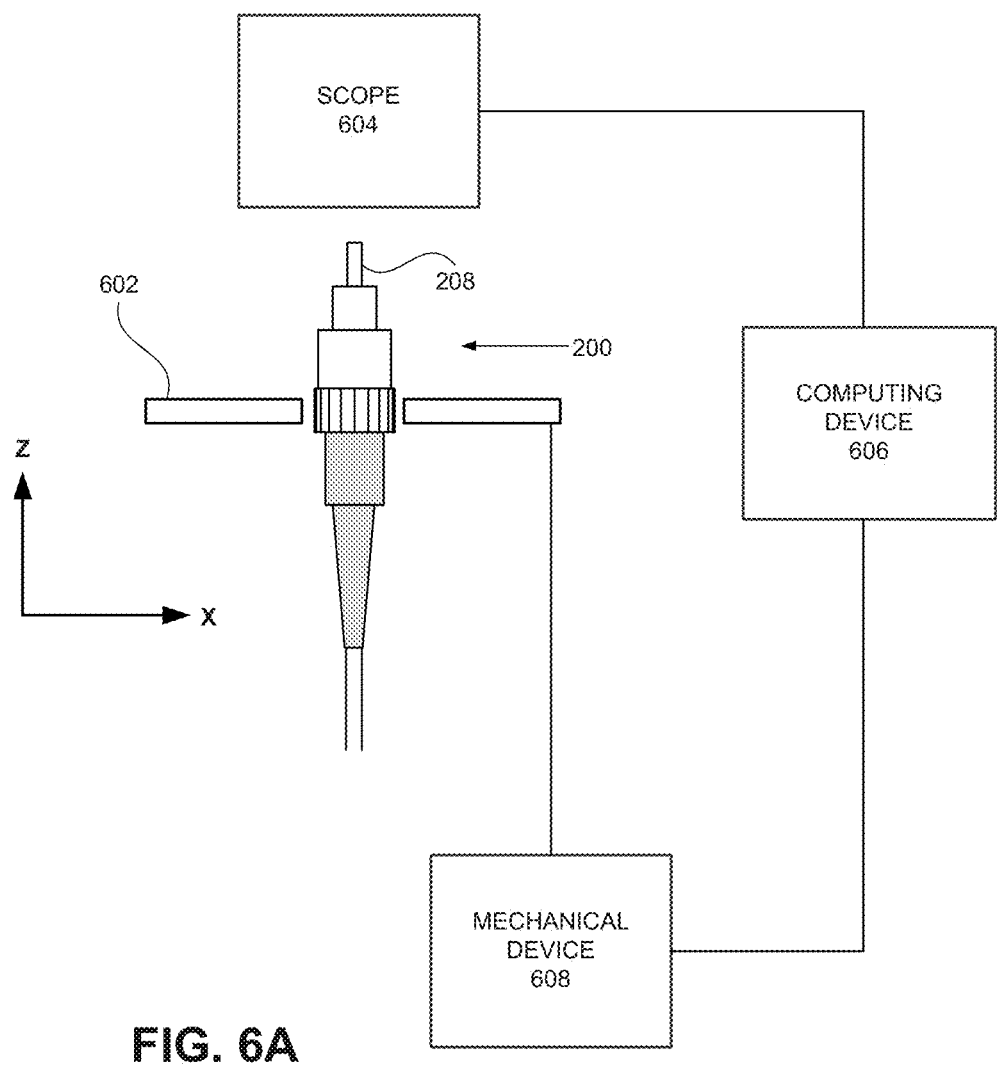
FIG. 6A illustrates an exemplary system for processing images of an end face of the optical fiber of FIG. 2A.

FIG. 6A illustrates an exemplary system 600 for processing images of the end face of ferrule 208 and optical fiber 210 to determine the opacity of the end face. As described above, depending on the implementation, the end face of ferrule 208/optical fiber 210 may have different geometries. As shown in FIG. 6A, system 600 may include a fiber optic connector mount 602, a fiber optic connector 200, a scope 604, a computing device 606, and a mechanical device 608.

Fiber optic connector mount 602 may include a structure on which fiber optic connector 200 may be stably mounted, such that scope 604 may obtain images of the end surface of ferrule 208 (and optical fiber 210, not visible in FIG. 6A) at desired magnifications. In some implementations, fiber optic connector mount 602 may be capable of moving in the direction of z-axis, x-axis, and y-axis (not shown), as well as rotate about the center axis of fiber optic connector 200 in the direction of z-axis.

Scope 604 may obtain one or more images of the end face of ferrule 208 and optical fiber 210 therein. Scope 604 may obtain the images at different magnifications (e.g., 800×, 400×, 200×, 100×, etc.) and send the images to computing device 606 in accordance with signals and/or instructions from computing device 606.

Computing device 606 may control devices and/or components of system 600. More specifically, computing device 606 may determine the type of optical contact associated with fiber optic connector 200 (e.g., APC, UPC, etc.) and may cause mechanical device 608 to orient fiber optic connector 200 for imaging the end face of optical fiber 210. In some implementations, computing device 606 may receive user input that indicates whether fiber optic connector 200 is an APC or UPC connector.

Figure 6B:
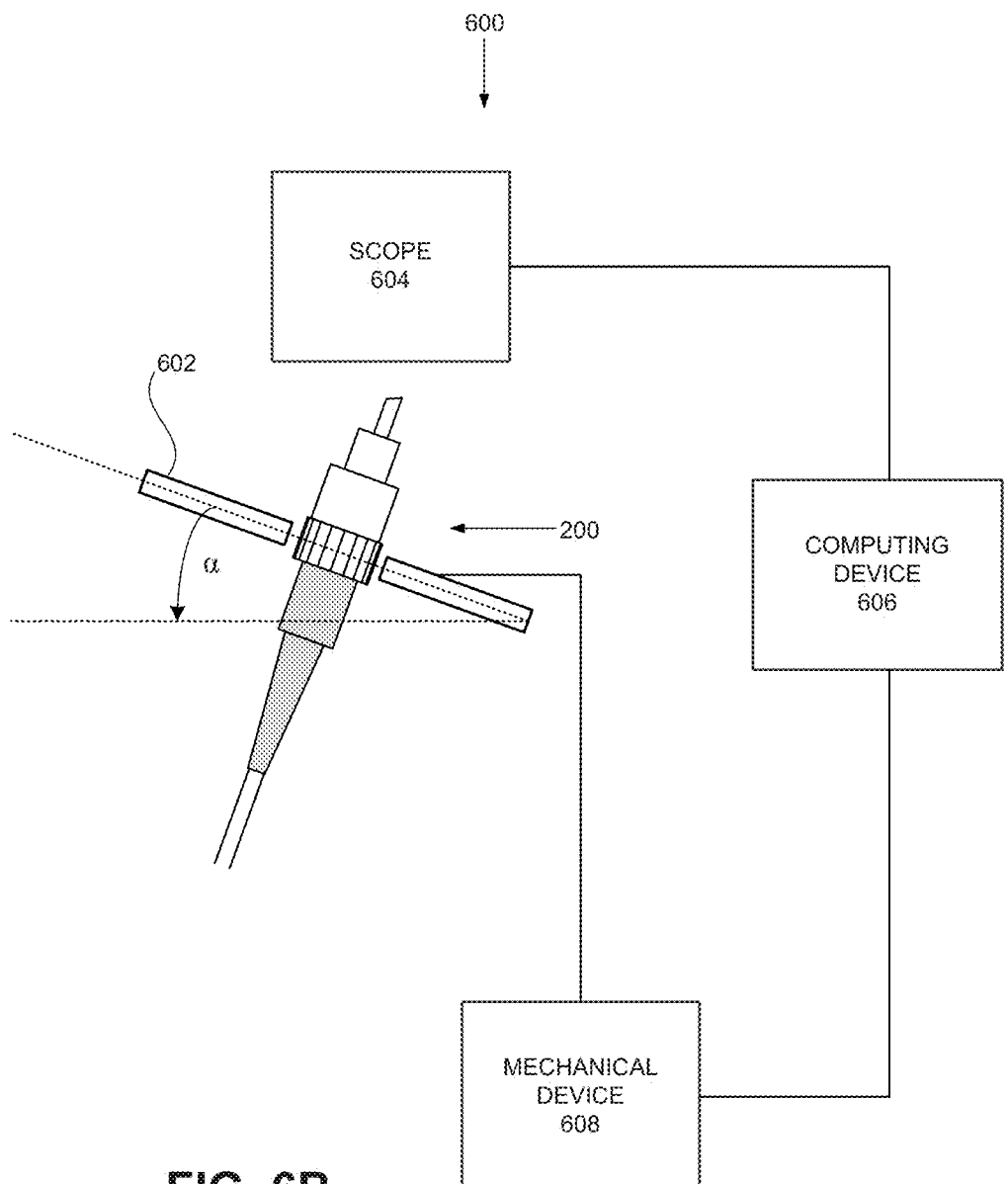
FIG. 6B illustrates the configuration of the system of FIG. 6A when the computing device of FIG. 6A determines that the fiber optic connector of FIG. 2A is an APC connector and orients the fiber optic connector for imaging the end face of the ferrule and the optical fiber in the fiber optic connector.

FIG. 6B illustrates the configuration of system 600 when computing device 606 determines or receives user input that fiber optic connector 200 is an APC connector and orients fiber optic connector 200 for imaging the end face of ferrule 208 and optical fiber 210. As shown, when fiber optic connector 200 is an APC connector, computing device 606 may cause mechanical device 608 to tilt fiber optic connector mount 602 by angle α degrees (e.g., 8 degrees). In other implementations, an operator or the user of system 600 may manually adjust the tilt of fiber optic connector mount.

Consistent with the implementations described herein, computing device 606 may determine the mode of optical fiber 210 inside fiber optic connector 200 (e.g., single mode fiber, multimode fiber, etc.) and may determine the opacity of the end face of optical fiber 210. Computing device 606 may determine the opacity by processing one or more images of the end face. The image processing may include identifying/recognizing scratches, damages, dirt, and/or other surface defects or characteristics (e.g., cleanliness) that impede the passage of optical signals through the end surface.

Mechanical device 608 may receive instructions and/or signals from computing device 606 and adjust the position and orientation of fiber optic connector 200 relative to scope 604.

System 600 is illustrated for simplicity. Although not shown, system 600 may include other components, such as a clamp, components for translating or orienting fiber optic connector 200, peripherals for computing device 606, etc. That is, depending on the implementation, system 600 may include additional, fewer, different, or differently arranged components than those illustrated in FIGS. 6A and 6B.

Figure 7:
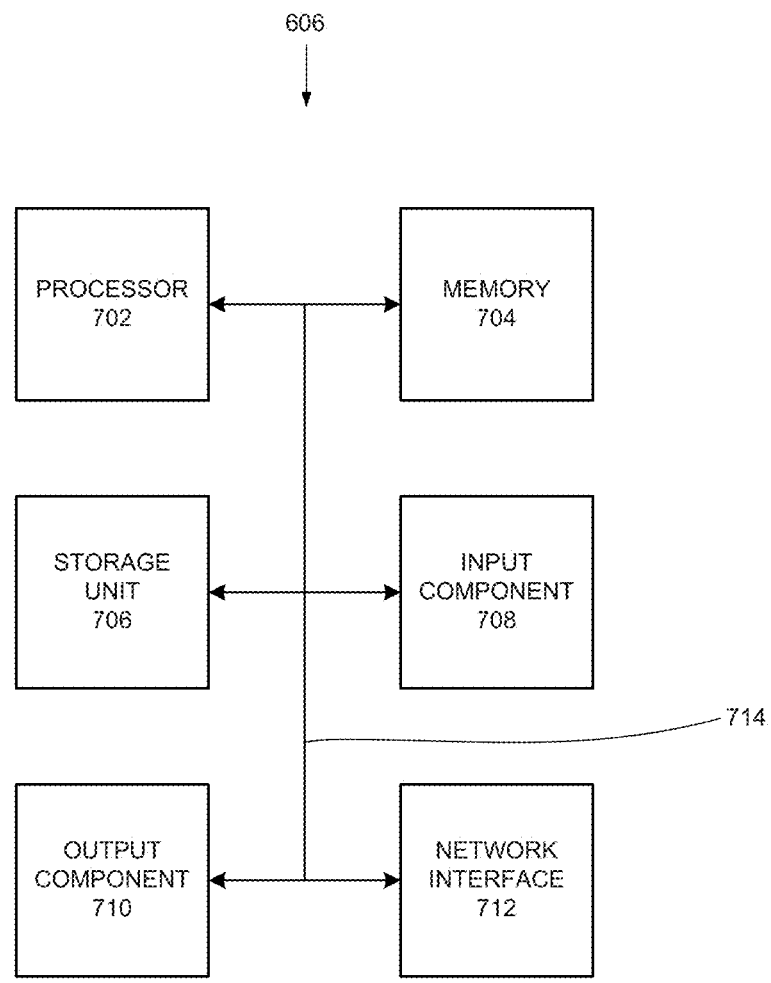
FIG. 7 is a block diagram of exemplary components of the computing device of FIGS. 6A and 6B.

FIG. 7 is a block diagram of exemplary components of computing device 606. As shown, computing device 606 may include a processor 702, memory 704, storage unit 706, input component 708, output component 710, network interface 712, and communication path 714. In different implementations, computing device 606 may include additional, fewer, different, or different arrangement of components than the ones illustrated in FIG. 7.

Processor 702 may include a processor, a microprocessor, an Application Specific Integrated Circuit (ASIC), a Field Programmable Gate Array (FPGA), and/or other processing logic (e.g., embedded devices) capable of controlling computing device 606.

Memory 704 may include static memory, such as read only memory (ROM), and/or dynamic memory, such as random access memory (RAM), or onboard cache, for storing data and machine-readable instructions (e.g., programs, scripts, etc.). Storage unit 706 may include a floppy disk, CD ROM, CD read/write (R/W) disc, and/or flash memory, as well as other types of storage devices (e.g., hard disk drive) for storing data and/or machine-readable instructions (e.g., a program, script, etc.). As used herein, the term "computer-readable medium" may include memory 704 and/or storage unit 706. Processor 702 may execute computer-readable instructions on a computer-readable medium, to perform different processes and serve functions that are associated with or described with respect to computing device 606.

Input component 708 and output component 710 may provide input and output from/to a user to/from computing device 606. Input/output components 708 and 710 may include a display screen, a keyboard, a mouse, a speaker, a microphone, a camera, a DVD reader, Universal Serial Bus (USB) lines, high definition media interface (HDMI), and/or other types of components for converting physical events or phenomena to and/or from signals that pertain to computing device 606.

Network interface 712 may include a transceiver (e.g., a transmitter and a receiver) for computing device 606 to communicate with other devices and/or systems. For example, via network interface 712, computing device 606 may communicate with mechanical device 608, or another device on a network to which computing device 606 is connected.

Communication path 714 may provide an interface through which components of computing device 606 can communicate with one another.

Figure 8:
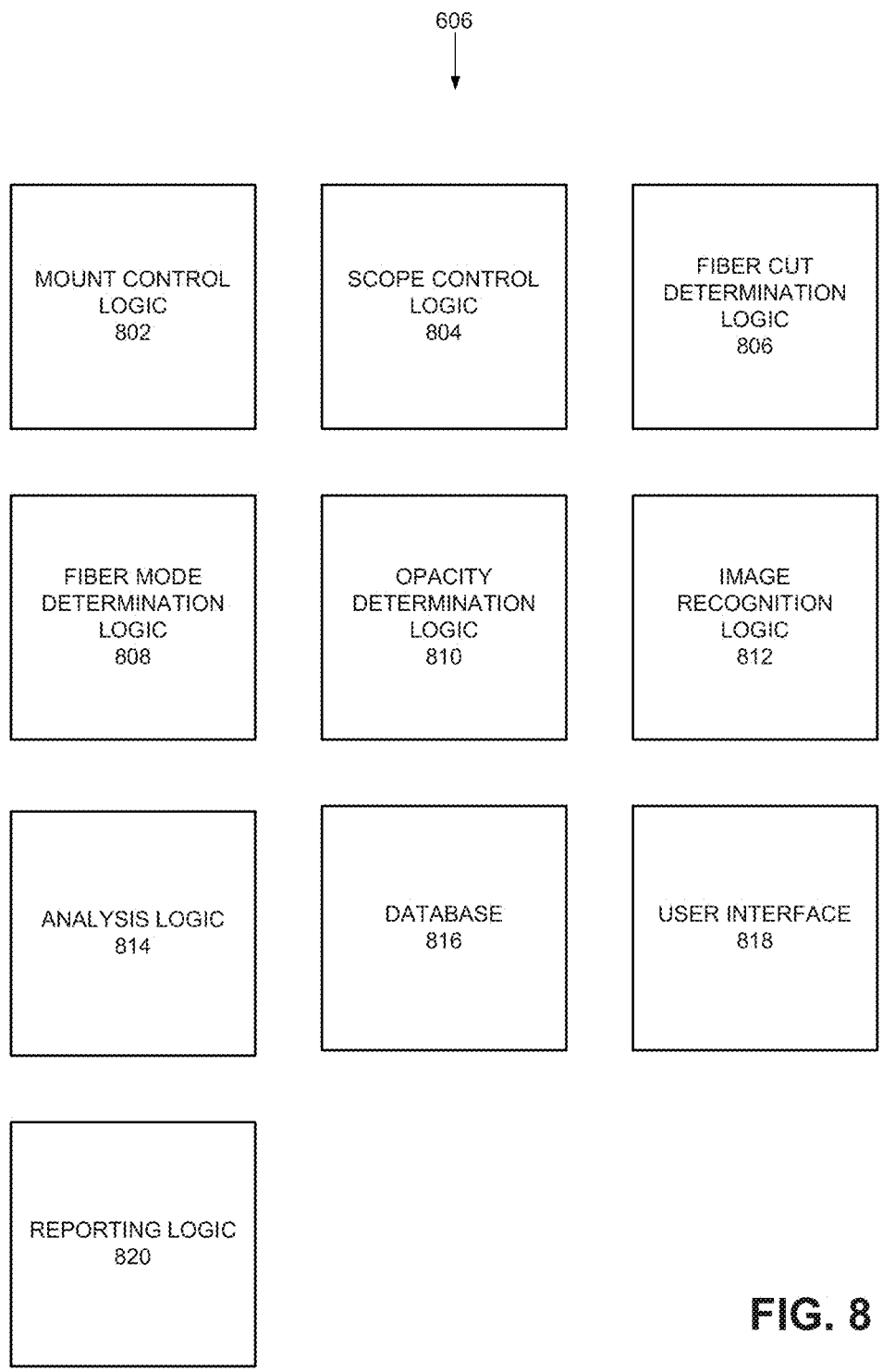
FIG. 8 is a block diagram of exemplary functional components of the computing device of FIGS. 6A and 6B.

FIG. 8 is a block diagram of exemplary functional components of computing device 606. As shown, computing device 606 may include mount control logic 802, scope control logic 804, fiber cut determination logic 806, fiber mode determination logic 808, opacity determination logic 810, image recognition logic 812, analysis logic 814, a database 816, a user interface 818, and reporting logic 820. Depending on the implementation, computing device 606 may include additional, fewer, different, or differently arranged components than those illustrated in FIG. 8. Furthermore, for simplicity, although computing device 606 may include other components, they are not illustrated in FIG. 8.

Mount control logic 802 may include hardware and/or software components for controlling the position and orientation of fiber optic connector mount 602. Mount control logic 802 may receive instructions from other logic of computing device 606, such as fiber cut determination logic 806, fiber mode determination logic 808, and opacity determination logic 810, and change the orientation and position of fiber optic connector mount 602 in accordance with the instructions. In some implementations, mount control logic 802 may receive control signals/instructions from a user via user interface 818.

Scope control logic 804 may include hardware and/or software components for controlling magnification of images, lighting, and/or other factors that are associated with capturing images of the end face of the ferrule of a fiber optic connector, Scope control logic 804 may receive instructions from other components of computing device 606, such as fiber cut determination logic 806, fiber mode determination logic 808, and/or opacity determination logic 810. In some implementations, mount control logic 802 may receive control signal/instructions from a user via user interface 818.

Fiber cut determination logic 806 may receive instructions from opacity determination logic 810 and/or user interface 818 and determine whether ferrule 208 of fiber optic connector 200 on fiber optic connector mount 602 is APC, UPC, or has an apex cut (e.g., see FIG. 4A). To determine the cut/contact, fiber cut determination logic 806 may capture images of the end face of ferrule 208. As fiber cut determination logic 806 captures the images (via scope 604), fiber cut determination logic 806 may instruct fiber optic connector mount 602 to move up or down, along the z-axis. If the focused portion (e.g., a portion of an image with the sharpest edges) changes from one captured image to another, fiber cut determination logic 602 may determine that fiber optic connector 200 is an APC connector. If the focused portion fades out from one image to another (or emerges), fiber cut determination logic 602 may determine that fiber optic connector 200 is UPC connector. If the focused portion yields a circular shape that becomes bigger or smaller from one image to another, fiber cut determination may determine that fiber optic connector 200 has an apex cut. Fiber cut determination logic 806 may provide a result of its determination to another component of computing device 606, such as opacity determination logic 810 or user interface 818. In some implementations, computing device 606 may determine the cut of fiber optic connector 200 based on user input (e.g., via user interface 818) rather than via fiber cut determination logic 806.

Fiber mode determination logic 808 may determine whether an optical fiber within ferrule 208 is a multimode or a single mode optical fiber. To determine whether an optical fiber is a single mode or a multimode optical fiber, fiber mode determination logic 808 may capture images of the end face of ferrule 208. Fiber mode determination logic 808 may identify ferrule 208, optical fiber 210, and core 222 in the images via image recognition logic 812. Furthermore, fiber mode determination logic 808 may determine the diameter of core 222. If the diameter is equal to the typical diameter of a multimode fiber, fiber mode determination logic 808 may conclude that optical fiber 210 is a multimode fiber. If the diameter is equal to the diameter of a single mode fiber, fiber mode determination logic 808 may conclude that optical fiber 210 is a single mode fiber. In some implementations, computing device 606 may determine the mode of optical fiber 210 based on user input (e.g., via user interface 818) rather than via fiber mode determination logic 808.

Opacity determination logic 810 may receive instructions from user interface 818 or another component and determine the opacity of optical fiber 210. To determine the opacity, opacity determination logic 810 may determine the cut of optical fiber 210 via fiber cut determination logic 806. If optical fiber 210 has an APC, opacity determination logic 810 may change the orientation of fiber optic connector mount 602 (e.g., via mount control logic 802), such that scope 604 may capture clear images of the end face of optical fiber 210. In addition, opacity determination logic 810 may control scope 604 to obtain clear (e.g., most focused) images.

After adjusting the position of fiber optic connector mount 602 and imaging parameters of scope 604, opacity determination logic 810 may determine whether optical fiber 210 is a multimode fiber or a single mode fiber, via fiber mode determination logic 808. In addition, opacity determination logic 810 may determine the location (within the captured images) of core 222 and cladding 224, as well as offset of core 222 and/or cladding 224 (e.g., eccentricity). Depending on whether optical fiber 210 includes a UPC or an APC, the shape of core 22s and cladding 224 may be circular or elliptical.

Consistent with the implementations described herein, opacity determination logic 810 may identify and classify different surface defects (e.g., scratches, film, dirt, reflective area, etc.) on the end face of optical fiber 210 via image recognition logic 812. Furthermore, for each of the identified surface defects, opacity determination logic 810 may obtain a set of parameters. For example, for a scratch, opacity determination logic 810 may determine the width of the scratch, the length of the scratch, its color, and its location(s) on the end-face area. For dirt, a film, or a reflective area, opacity determination logic 810 may determine the size (e.g., a diameter), location, and color.

When requested by another component or a user or on its own, opacity determination logic 810 may provide or store the following: the locations of surface defects within the given image of an end face; one or more images of the recognized surface defects within the given image; a shape of the end face (e.g., a circle or oval (e.g., for fiber optic connectors with APCs)); fiber optic/cladding offset (e.g., apex offset 408); the size of core 222; for each defect, the type of defect (e.g., a scratch, film, dirt, large particle, reflective area, etc.); the type of mode of the fiber (e.g., multimode or a single mode), etc.

In determining signal degradation due to surface defects, opacity determination logic 810 may divide the end face of optical fiber 210 into a circular area (near the center of optical fiber 210) and concentric bands of different radii. Depending on which area or band a particular surface defect is located in, the surface defect may contribute to different amounts of signal degradation. For example, assume that a surface defect in the circular area is near core 222, and that the surface defect may causes the signal to degrade by X dB. If the surface defect is near an outer band (near cladding 224), the surface defect may cause the signal to degrade by Y dB, where X>Y.

In another example, assume that a first scratch within the end face area associated with core 222 causes 10 dB degradation per unit length. Then, a second scratch similar to the first scratch, but within a band on the end face area corresponding to cladding 224, may cause 2 dB degradation. Given the length of a scratch and the location of the scratch (e.g., whether the scratch is in the area corresponding to core 222 or is in the area corresponding to cladding 224), opacity determination logic 810 may determine the signal degradation at the end face due to surface defects. Opacity determination logic 810 may perform similar types of analysis with different types of end face defects, to arrive at the opacity (measured as dB loss) at the end face of optical fiber 210.

Depending on the mode of the fiber (e.g., multimode or single mode), opacity determination logic 810 may divide the end-face area in different ways, for the purpose of obtaining the signal degradation or determining the opacity. For example, assume that opacity determination logic 810 is determining the opacity due to defects on the end face of a multimode fiber. An area (obtained from dividing the end-face area of the multimode fiber into different areas) near the core of multimode fiber would be larger than a corresponding or similar area of a single mode fiber.

For fiber optic connectors with APCs, the shape of end-face area of optical fiber 210 is elliptical. Accordingly, for fiber optic connectors with APCs, opacity determination logic 810 may divide the end-face area of optical fiber 210 into an elliptical area (near the center) and concentric bands of ellipses with different major diameters. Surface defects that are near the core of optical fiber 210 would contribute more to degradation of optical signals passing through the end face.

Image recognition logic 812 may recognize different features within a given image. For example, image recognition logic 812 may recognize the image of core 222, the end face of optical fiber 210, surface defects, etc. When image recognition logic 812 receives a request to identify a feature(s) within a given image (e.g., image of ferrule 208) from a logical component (e.g., logic 810), image recognition logic 812 may retrieve an image or data associated with the feature from database 816 and use the retrieved image/data to identify the feature within the given image.

Analysis logic 814 may receive different types of requests from a user, via user interface 816, or another component, to provide information about optical fiber 210 or another component (e.g., ferrule 208). In response, analysis logic 814 may obtain the information and provide the information to the user or the other component. The information may include an insertion loss, a return loss, any information stored by opacity determination logic 810 in database 816, etc. The information may also include the number of defects in a region within an end face (e.g., area associated with core, area associated with cladding, etc.). In some instances, analysis logic 814 may provide recommendations for high power use of the tested fiber optic connector 200 or lower power system sensitivity warnings.

When analysis logic 814 may is requested to provide an insertion loss and/or return loss, analysis logic 814 may determine, via opacity determination logic 810, how much loss the surface defects may contribute to signal degradation, based on information on the surface defects. In addition, analysis logic 814 may determine additional losses based on the offset of fiber core/cladding (e.g., apex offset 408).

In some implementations, analysis logic 814 may provide, in addition to the estimations of the insertion loss and return loss, multi-path interference predictions. For multimode fibers, analysis logic 814 may be able to determine the extent of mode coupling, as well as the insertion loss and return loss.

Database 816 may include data/images associated with optical fiber 210, fiber optic connector 200, and surface defects of the end face of optical fiber 210 or a ferrule 208. In some instances, the data may also include a corresponding insertion loss and return loss that are input by users or obtained from experiments. Presented with defects of a fiber optic connector 200, database 816 may retrieve identifies of other fiber optic connectors whose end-face defects are similar.

Database 816 may be available from a field (e.g., over a network) or from within a lab for testing and comparison/correlation of stored data to measured data. Database 816 may be updated (e.g., insert additional records or remove records associated with a fiber optic connector) as new data becomes available.

User interface 818 may include one or more software components for interacting with different components of computing device 606 and/or system 600. For example, user interface 818 may allow the user, via the components of computing device 606, to move or reorient fiber optic connector mount 602, control scope 604, run analysis logic 814, search through database 816, and/or save data in database 816.

Reporting logic 820 may dispatch data, emails, and/or other communications to users and/or operators of system 600, to convey results of processing and analyzing images of one or more fiber optic connectors.

Figure 9:
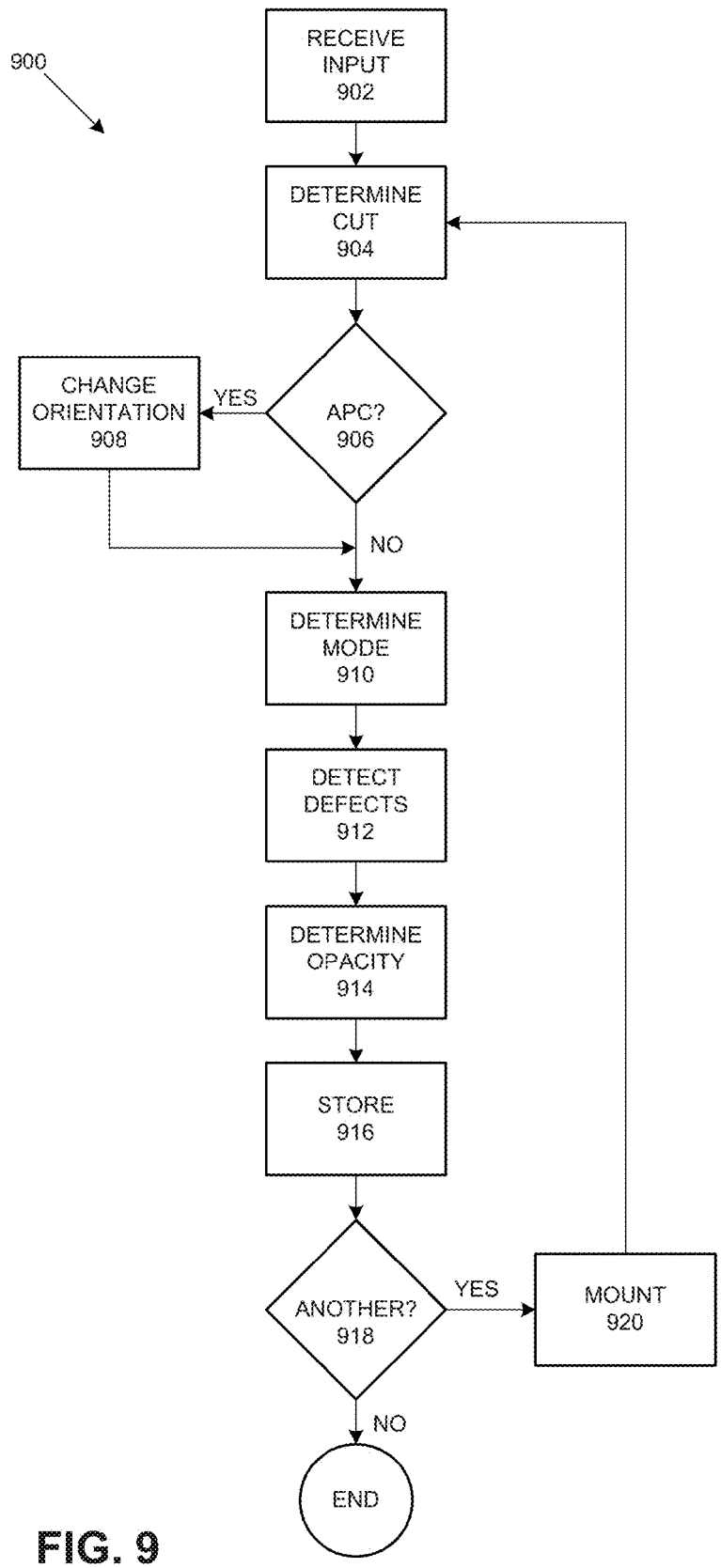
FIG. 9 is a flow diagram of an exemplary process associated with the system of FIGS. 6A and 6B.

FIG. 9 is a flow diagram of an exemplary process 900 that is associated with system 600. Assume that fiber optic connector 200 is mounted on fiber optic connector mount 602 as illustrated in FIG. 6. In addition, assume that certain constraints on end-face geometry of ferrule 208 are satisfied. For example, assume that each of undercut 502 and overcut 504 (the protrusion) of optical fiber 210 in ferrule 208 (see FIGS. 4C and 4D) is less than 100 nanometers (nm).

Process 900 may include computing device 606 receiving user input (block 902). The user input may request opacity determination logic 810 or analysis logic 816 to determine the opacity of optical fiber 210 housed inside fiber optic connector 200. In response to the user input, computing device 606 may determine the cut/contact (e.g., APC, UPC, or apex cut) of ferrule 208/optical fiber 210 in fiber optic connector 210 (block 904). As described above, computing device 606 may determine the cut or the contact via fiber cut determination logic 806 (block 906).

If optical fiber 210 includes an APC (block 906: yes), computing device 606 may change the orientation of fiber optic connector 200 so that the end face of optical fiber 210 is parallel to the viewing plane of scope 604 (block 908). Thereafter, computing device 606 may proceed to block 910. At block 906, if optical fiber 210 does not include an APC (block 906: no), computing device 606 may proceed directly to block 910.

Computing device 606 may determine the mode of optical fiber 210 (block 910). As described above, computing device 606 may determine the mode of optical fiber 210 by identifying core 222 on the end face of optical fiber 210 and by determining the size of core 222. For example, if the size of core 222 is approximately equal to the size of a typical multimode fiber, computing device 606 may determine that optical fiber 210 is a multimode fiber. If the size of core 222 is approximately equal to the size of a typical single mode fiber, computing device 606 may determine that optical fiber 210 is a single mode fiber.

Computing device 606 may detect or identify scratches, films, dirt, reflective areas, and/or other types of surface defects on the end face of optical fiber 210 (block 912). In addition, computing device 606 may detect other features, such as eccentricity (e.g., apex offset). Computing device 606 may detect the surface defects or other features of optical fiber 210 based on image recognition. In detecting each of the surface defects/the other features, computing device 606 may also determine properties that are associated with each surface defect/feature (e.g., length and width of a scratch, the color of film/dirt, the diameter of the core, etc.).

Computing device 606 may determine the opacity of the end face (e.g., end face 402) of optical fiber 210 based on the surface defects on the end face of optical fiber 210 (block 914). Determining the opacity of optical fiber 210 may include determining signal degradations caused by the identified surface defects within each of the end face areas (e.g., areas corresponding to core 222 and cladding 224, etc) and aggregating the degradations over the end face. As described above, degradation associated with a defect may depend on an area, within the end face, in which the defect is located, the color and size of the defect, etc.

In some implementations, computing device 606 may determine the insertion loss and return loss of fiber optic connector 200, by combining the loss associated with the opacity) with losses due to other factors, such as losses due to the offset of the center of the core/optical fiber relative to the center of ferrule 208.

Computing device 606 may store and/or display the result of the analysis (e.g., determined opacity, insertion loss, return loss, etc.), along with other information associated with fiber optic connector 200 (block 916). For example, given fiber optic connector 200, computing device 606 may display or store information related to the surface defects (e.g., images of the scratches, dirt, film, reflective areas, cracks, etc.), the mode of optical fiber 210, the cut/contact of optical fiber 210, the opacity, etc. in database 816.

In some implementations, system 600 may be capable of processing images of and analyzing multiple fiber optic connectors. In such implementations, at block 916, computing device 606 may determine if there is another fiber optic connector 200 that may be analyzed (block 918). If there is another fiber optic connector to be examined/analyzed (block 918: yes), computing device 606 may cause mechanical device 608 to remove fiber optic connector 200 from fiber optic connector mount 602 and mount the other fiber optic connector in fiber optic connector mount 602. Thereafter, computing device 606 may proceed to block 902 or 904 (an arrow to 902 not shown). If there is no more fiber optic connector to be examined/analyzed (block 916: no), computing device 606 may end process 900.

As described above, system 600 may process images of the end face of optical fiber 210 housed in fiber optic connector 200. Given fiber optic connector 200, system 600 may determine the type of optical contact/cut associated with the fiber optic connector (e.g., APC, UPC, apex cut); may position fiber optic connector 200 for imaging the end face of optical fiber 210 housed in fiber optic connector 200; may determine the type of optical fiber 210 inside fiber optic connector 200 (e.g., single mode fiber or multimode fiber); and may determine the opacity of the end face of optical fiber 210. System 600 may determine the opacity by processing one or more images of the end face. The image processing may include identifying scratches, damages, and/or other surface defects that impede propagation of optical signals through the end face.

In this specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

While a series of blocks have been described with regard to the process illustrated in FIG. 9, the order of the blocks may be modified in other implementations. In addition, non-dependent blocks may represent blocks that can be performed in parallel.

It will be apparent that aspects described herein may be implemented in many different forms of software, firmware, and hardware in the implementations illustrated in the figures. The actual software code or specialized control hardware used to implement aspects does not limit the invention. Thus, the operation and behavior of the aspects were described without reference to the specific software code—it being understood that software and control hardware can be designed to implement the aspects based on the description herein.

No element, block, or instruction used in the present application should be construed as critical or essential to the implementations described herein unless explicitly described as such. Also, as used herein, the article "a" is intended to include one or more items. Further, the phrase "based on" is intended to mean "based, at least in part, on" unless explicitly stated otherwise.

What is claimed is:

1. A system comprising:
   a scope for obtaining images of an end face of an optical fiber in a fiber optic connector;
   a mechanical device configured to orient the fiber optic connector; and
   a computing device configured to:
      determine a type of contact of the optical fiber;
      cause the mechanical device to orient the fiber optic connector such that the end face of the optical fiber is parallel to a plane that is imaged by the scope when the type of contact of the optical fiber is an angle polished contact;
      obtain images of the end face of the optical fiber via the scope;
      identify surface defects on the end face of the optical fiber based on the images; and
      determine insertion loss of the fiber optic connector due to the surface defects.

2. The system of claim 1, wherein the computing device is further configured to cause the scope to obtain one or more images of the end face at 400× magnification.

3. The system of claim 1, wherein the computing device is further configured to:
   determine whether each of the surface defects is on an area, in the end face, that corresponds to a core of the optical fiber or an area, in the end face, that corresponds to a cladding of the optical fiber.

4. The system of claim 3, wherein when the computing device determines the insertion loss, the computing device is configured to:
   determine, for each of the surface defects, an amount of signal degradation that the surface defect causes based on the determination whether the surface defect is on the area that corresponds to the core of the optical fiber or the area that corresponds to the cladding.

5. The system of claim 1, wherein the surface defects include at least one of:
   a scratch, a crack, or dirt.

6. The system of claim 5, wherein when the computing device identifies the surface defects, the computing device is further configured to:
   identify the scratch, the crack or the dirt on the end face based on image recognition; and
   determine at least one of a location or a size of the scratch, the crack, or the dirt.

7. The system of claim 1, wherein the computing system is further configured to:
   identify a core of the optical fiber in images of the end face of the optical fiber;
   determine a diameter of the core; and
   determine whether the optical fiber is a multimode fiber or a single mode fiber based on the diameter of the core.

8. The system of claim 7, wherein when the computing device determines whether the optical fiber is a multimode fiber or a single mode fiber, the computing device is further configured to:
   determine whether the diameter of the core is approximately equal to a typical diameter of a multimode fiber or a typical diameter of a single mode fiber.

9. The system of claim 1, wherein the computing device is further configured to:
   obtain images of the end face of a ferrule of the fiber optic connector; and
   determine whether the fiber optic connector includes an angle polished contact, an ultra polished contact, or an apex contact based on the images.

10. The system of claim 1, wherein the computing device determines whether the fiber optic connector includes an angle polished contact, an ultra polished contact, or an apex contact based on a user provided input at the computing device.

11. The system of claim 1, wherein the computer device is further configured to:
    determine an eccentricity of the optical fiber; and
    determine the insertion loss of the fiber optic connector due to the surface defects and the eccentricity.

12. A device comprising:
    an interface for communicating with an external device;
    a memory configured to store program instructions; and
    one or more processors to execute the program instructions to:
       determine a type of contact of an optical fiber being housed in a fiber optic connector;
       cause a device holding the fiber optic connector to reorient the fiber optic connector, such that an end face of the optical fiber is parallel with a plane of a view of a scope communicatively coupled wirelessly or via wires to the interface, when the fiber optic connector is an angle polished contact connector;
       obtain images of the end face of the optical fiber from the scope;
       identify surface defects on the end face of the optical fiber based on the images; and
       determine power loss of the fiber optic connector due to the surface defects.

13. The device of claim 12, wherein the surface defects includes one of:
    a scratch or a crack in the end face.

14. The device of claim 12, wherein the one or more processors are further configured to:
    determine whether each of the surface defects is on an area, on the end face, that corresponds to a core of the optical fiber.

15. The device of claim 12, wherein when the one or more processors identify the surface defects, the one or more processors are configured to:
    identify a scratch or a crack on the end face based on image recognition; and
    determine at least one of a location or a size of the scratch or the crack.

16. The device of claim 12, wherein the one or more processors are further configured to:
    identify a core of the optical fiber in images of the end face of the optical fiber;
    determine a diameter of the core; and
    determine whether the optical fiber is a multimode fiber or a single mode fiber based on the diameter of the core.

17. The device of claim 12, wherein the one or more processors are further configured to:
    obtain images of the end face of a ferrule of the fiber optic connector; and
    determine whether the fiber optic connector includes an angle polished contact (APC), an ultra polished contact (UPC), or an apex contact based on the images.

18. The device of claim 12, wherein the power loss includes at least one of:
    insertion loss or return loss.

19. The device of claim 12, wherein the one or more processors are further configured to:
    determine an eccentricity of the optical fiber; and
    determine the power loss of the fiber optic connector due to the surface defects and the eccentricity.

20. A non-transitory computer-readable medium including computer executable instructions, when executed by one or more processors, cause the one or more processors to:
    obtain one or more images of an end face of an optical fiber from a scope;
    determine whether the optical fiber is a multimode optical fiber or a single mode optical fiber;
    identify surface defects on the end face of the optical fiber based on the images;
    determine insertion loss of the fiber optic connector due to the surface defects based on the identification of the surface defects and based on the determination of whether the optical fiber is a multimode optical fiber or a single mode optical fiber.

21. The non-transitory computer-readable medium of claim 20, further comprising instructions, when executed by the one or more processors, cause the one or more processors to:
    determine whether the fiber optic connector is an angle polished contact (APC) connector, an ultra polished contact (UPC) connector, or an apex contact connector based on images of a ferrule of the fiber optic connector.

* * * * *